(12) United States Patent
Hall et al.

(10) Patent No.: US 10,542,937 B2
(45) Date of Patent: Jan. 28, 2020

(54) INTELLIGENT HEALTH MONITORING TOILET SYSTEM WITH WAND SENSORS

(71) Applicants: David R. Hall, Provo, UT (US); Joe Fox, Spanish Fork, UT (US)

(72) Inventors: David R. Hall, Provo, UT (US); Joe Fox, Spanish Fork, UT (US)

(73) Assignee: Hall Labs LLC, Provo, UT (US)

( * ) Notice: Subject to any disclaimer, the term of this patent is extended or adjusted under 35 U.S.C. 154(b) by 0 days.

(21) Appl. No.: 15/644,149

(22) Filed: Jul. 7, 2017

(65) Prior Publication Data
US 2019/0008457 A1    Jan. 10, 2019

(51) Int. Cl.
| | |
|---|---|
| A61B 5/00 | (2006.01) |
| A61B 5/01 | (2006.01) |
| A61B 10/00 | (2006.01) |
| A61B 5/11 | (2006.01) |
| A61B 90/30 | (2016.01) |
| E03D 11/13 | (2006.01) |
| A47K 13/24 | (2006.01) |
| E03D 9/08 | (2006.01) |

(52) U.S. Cl.
CPC ............ *A61B 5/6891* (2013.01); *A47K 13/24* (2013.01); *A61B 5/01* (2013.01); *A61B 5/1128* (2013.01); *A61B 10/00* (2013.01); *A61B 90/30* (2016.02); *E03D 9/08* (2013.01); *E03D 11/13* (2013.01); *A61B 5/0075* (2013.01); *A61B 5/0077* (2013.01); *A61B 2010/0083* (2013.01)

(58) Field of Classification Search
CPC ...................................................... A47K 13/24
USPC .............................................................. 4/420
See application file for complete search history.

(56) References Cited

U.S. PATENT DOCUMENTS

| | | | | |
|---|---|---|---|---|
| 5,493,737 A * | 2/1996 | Chu | ........................ | E03D 9/052 |
| | | | | 4/213 |
| 9,828,755 B1 * | 11/2017 | Clements | ................... | E03D 9/08 |
| 2015/0059076 A1 * | 3/2015 | Tiagai | .................... | G06T 1/0014 |
| | | | | 4/447 |

* cited by examiner

*Primary Examiner* — Lauren A Crane (57) ABSTRACT

The health monitoring toilet system includes an extendable, retractable, and rotatable wand with sensors on the head section. The sensors may include a variety of cameras and gas sensors for inspecting a user's urogenital, perineal, and anal region for health assessment. The wand may comprise a bidet wand. The bidet wand may also dispense cleansing and therapeutic substances. The toilet system may include a controller which may store the sensor readings as well as protocols for moving the wand to acquire optimal sensor readings. The controller may be accessible by a healthcare provider for diagnostic and treatment purposes. The toilet system may identify each user to store sensor reading acquired for different users in the controller.

19 Claims, 6 Drawing Sheets

INTELLIGENT HEALTH MONITORING TOILET SYSTEM WITH WAND SENSORS

BACKGROUND

Field of the Invention

This invention relates to methods and devices for assessing the health status of an individual and providing a diagnosis of disease Background of the Invention Toilets are ubiquitous devices which are used every day, often multiple times per day. By placing health monitors in a toilet, certain aspects of a user's health may be conveniently and discretely monitored each day and correlations can be made by comparing health data collected from each use. Diagnostic information that might go unnoticed during a single visit to a healthcare provider could be determined through daily observations.

A moving medical device within the toilet would be useful to thoroughly scan the urogenital, perineal, and anal areas of a user and collect health information relating to this area of a user's anatomy. For example, a moving wand may comprise a bidet wand to cleanse the user as well as collect health data as it moves beneath a user seated on the toilet. A wand system is needed which may comprise a bidet wand that, in addition to cleansing functions, collects heath data from a user each time the user is seated on the toilet.

BRIEF SUMMARY OF THE INVENTION

We disclose a health monitoring toilet system that includes an extendable, retractable, and rotatable wand. The wand may have one or more sensors which may include still, infrared, or video cameras. The sensors may include a gas sensor for detecting volatile organic compounds and temperature sensors. A temperature sensor may also be present within the toilet bowl to detect the temperature of the toilet water in the toilet bowl.

The wand may include a light source to provide light for the cameras. Alternatively, the light source may be positioned elsewhere in the toilet bowl.

The wand may include a dispenser for water and spray ports for dispensing cleansing or therapeutic substances. The cleansing or therapeutic substances may be stored in reservoirs and the substances may be transported from the reservoirs to the wand through conduits.

The toilet system may include a controller which may receive and process data from the sensors on the wand. The controller may include non-transitory computer readable medium, which may store data collected by the sensors for each user.

The wand may be moved, including extending, retracting, or rotating, according to a wand positioning system. The wand positioning system may include a wand movement device and a wand movement protocol. The wand movement protocol may be stored in the non-transitory computer readable medium. Wand movement protocols may be customized for individual users as customized user settings and may be altered manually through a manual control input interface or through wireless or other electronic methods. A healthcare provider may also have access to modify the wand movement protocol for certain users.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings.

DETAILED DESCRIPTION OF THE INVENTION

Definitions

User, as used herein, means an individual, human or animal, from which the disclosed system collects health-related information.

Healthcare provider, as used herein, means any individual who performs a task, mental or physical, in relation to health-related services provided to a user. In addition to clinicians who practice medicine directly on a user, the term healthcare provider includes any person that enters data into a computer or manages the data, when the data is used in analysis of a user's health status or to improve a user's health.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

Figure 1:
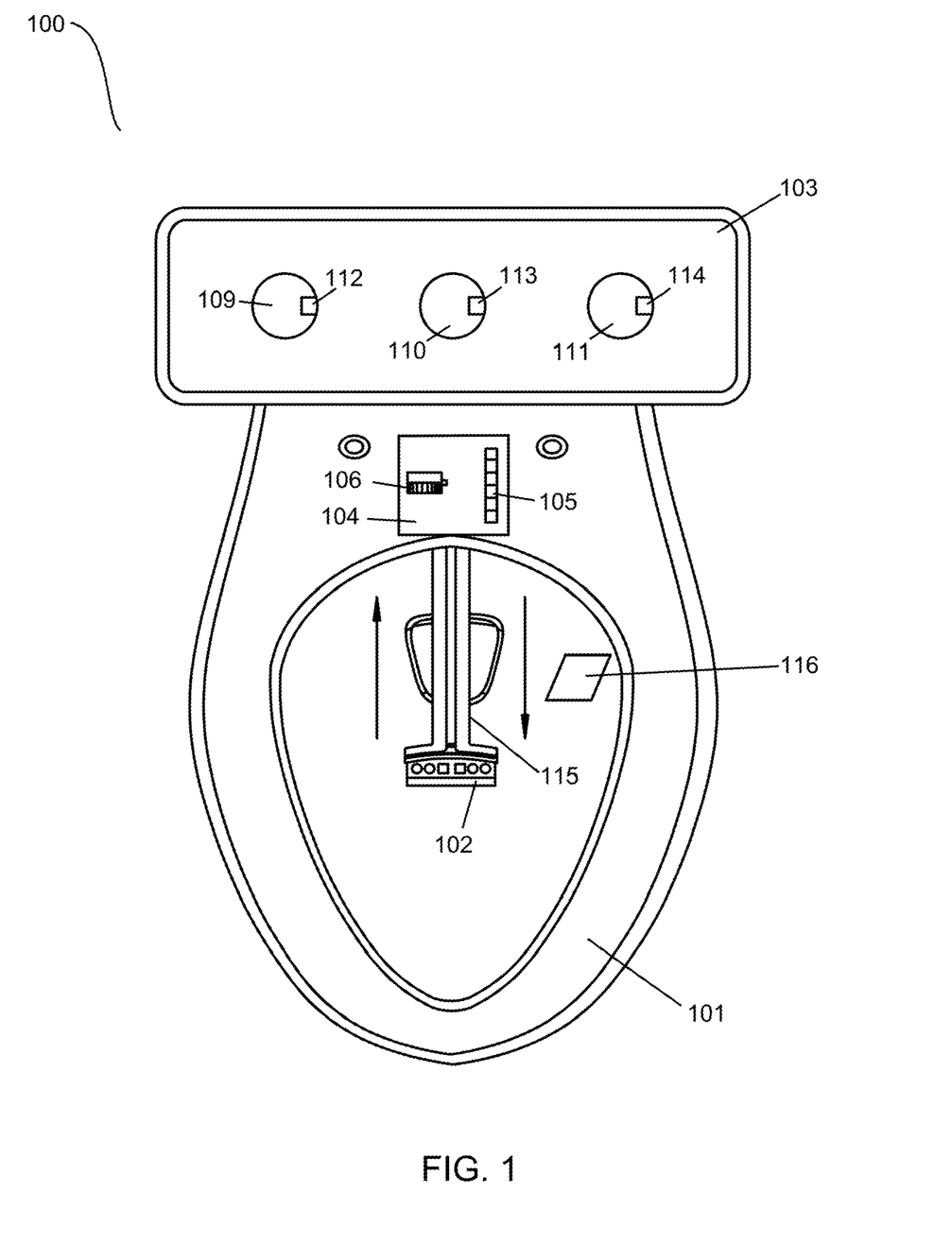
FIG. 1 illustrates an aerial view of an embodiment of the disclosed health monitoring toilet system.
Figure 2:
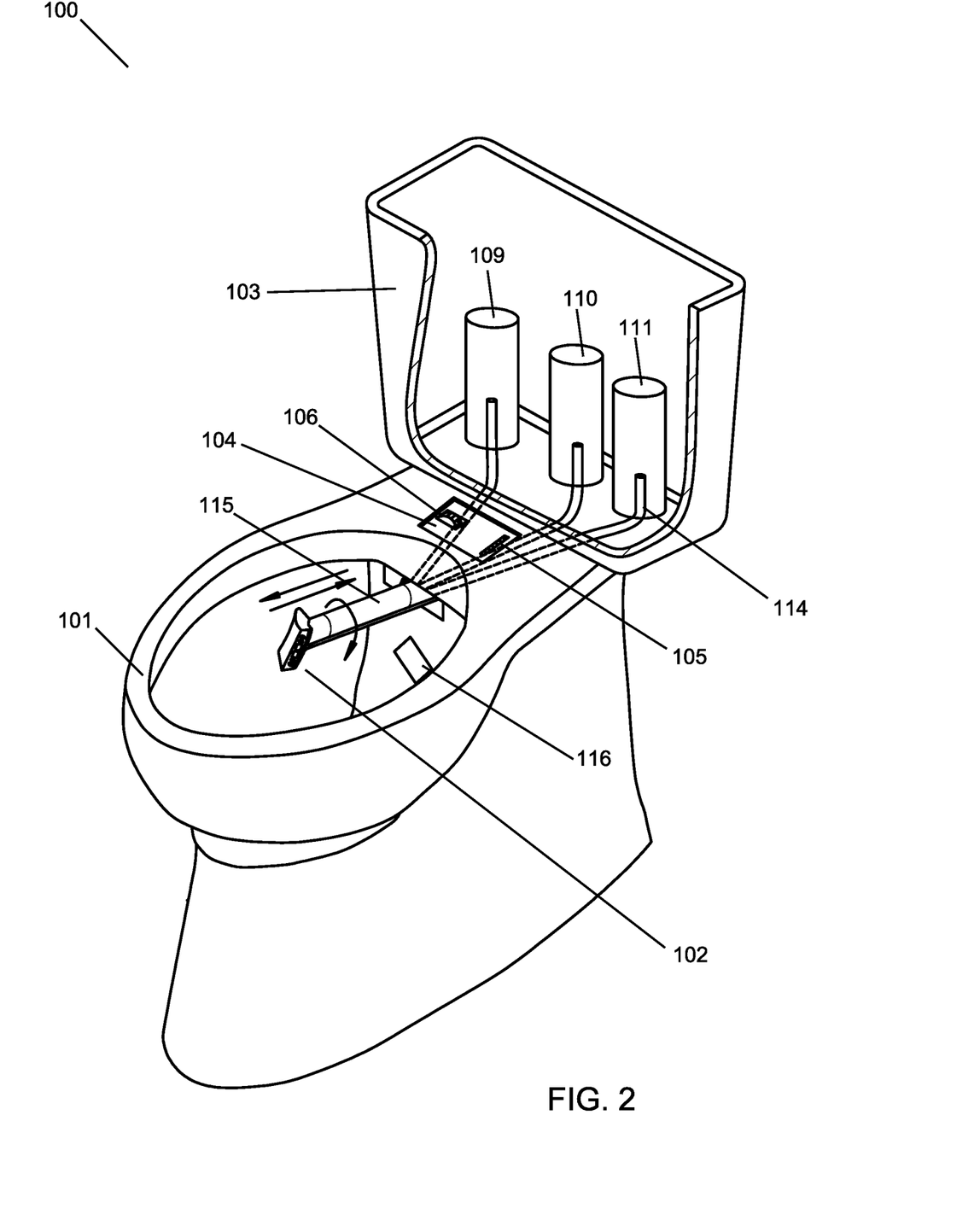
FIG. 2 illustrates an isometric view of toilet system of FIG. 1.

Referring to FIGS. 1 and 2, toilet apparatus 100, in accordance with the disclosure, is illustrated. Toilet apparatus 100 includes toilet rim 101 and tank 103. For clarity, toilet apparatus 100 is illustrated without a toilet seat or a toilet tank lid. A wand, including a bidet wand, may comprise head section 102 and ridged body section 115, is shown in an extended position. Head section 102 may rotate to any angle from 0-360 degrees. Accordingly, head section 120 may inspect, observe, analyze, cleanse, and treat a user's urogenital, perineal, and anal area from a variety of angles.

Reservoirs 109, 110, and 111 may house different cleansing or therapeutic substances. The cleansing or therapeutic substances may be transported from reservoirs 109, 110, and 111 into the wand through tubing 112, 113, and 114 respectively. Tubing 112, 113, and 114 may deliver the cleansing or therapeutic substances into rigid body section 115. Head section 102 may employ multiple spray ports (shown in more detail in FIGS. 4 and 6) through which to dispense the cleansing or therapeutic substances. Head section 102 may also include multiple sensors. The sensors may include, but are not limited to, one or more of the following: an optical sensor, an infrared camera, a gas sensor, a digital imaging device, a temperature sensor, an optical transmitter/receiver pair, a video camera, or a still photo camera. The gas sensor may detect volatile organic compounds which may be useful for diagnostic purposes.

Head section 102 may rotate according to a manually entered command through a manual control input interface, shown as input panel 104, or according to a wand movement protocol stored within the non-transitory computer readable medium. The wand movement protocol may be part of a wand positioning system and may be stored in the controller. The wand positioning system may further include a wand movement device. The wand movement device may include motors, linear actuators, screw drives, solenoids, belt drives, direct drives, pinion gears, or manual actuation. The wand movement device may include a tilting member and actuator for tilting ridged body section 115 and head section 102 as directed by the wand movement protocol. The wand movement device may also include a rotational device for rotating the head section 102 and/or ridged body section 115. In addition to modification made by the user, a healthcare provider may have access to stored wand movement protocols. This may be useful when the healthcare provider wishes to conduct a specific analysis of a specific user.

The sensors and spray ports may be in any location and configuration on head section 102 or rigid body section 115 of the wand. The spray ports may rotate or spray directionally applying various amounts of pressure. For example, the spray ports may include an oscillatory spray nozzle or rotating spray nozzle. Observation and inspection through visible, ultraviolet, or infrared, florescence, or optical inspection may be used to observe, record, and analyze tissue swelling, coloration, color variation, temperature, temperature variation, sores, skin condition, or skin texture (i.e. roughness). Visual inspection may also be employed through a live video feed to a user's phone, computer, handheld control, or to a controller accessible to a healthcare provider. Observation and inspection may also be done at a later time. For example, the sensors may transmit the data they collect to a non-transitory storage medium in the controller where the data may be stored. Alternatively, the data the sensors collect may be transmitted to a network storage device, or to a cloud based storage account. For clinical use, a healthcare provider may access these recorded observations from the storage location. The healthcare provider may then analyze the condition of the user based on the recorded observations, which may include but are not limited to; body temperature, waste temperature, tissue swelling, tissue coloration, tissue coloration variation, sores, skin texture. The continual recording of these observations may allow the healthcare provider to compare recorded observations over time and appreciate changes in the user's condition.

Upon detection of an unclean area on the user's urogenital, perineal, or anal areas, the wand comprising a bidet wand may cleanse the area either for therapeutic or hygienic purposes or to provide clearer detection of the region by the sensors. The spray ports may be automatically or manually directed towards an area which is in need of cleansing. The spray ports are described in greater detail with reference to FIGS. 4 and 6. Input panel 104 contains wand extender control 105 which a user may manually operate to extend or retract the wand based on user preference. Head rotator control 106 is shown as a dial which a user may move left or right to manually rotate head section 102. Input panel 104 may be part of a wand positioning system which also includes a wand movement device. The wand movement device may include motors, linear actuators, screw drives, solenoids, belt drives, direct drives, pinion gears, or manual actuation. The wand movement device may include a tilting member and actuator for tilting ridged body section 115 and head section 102. The wand movement device may also include a rotational device for rotating the head section 102 and/or ridged body section 115. The positioning and tracking system may incorporate vision system feedback for control and identification of regions of interest on a user or in a toilet bowl.

Figure 3:
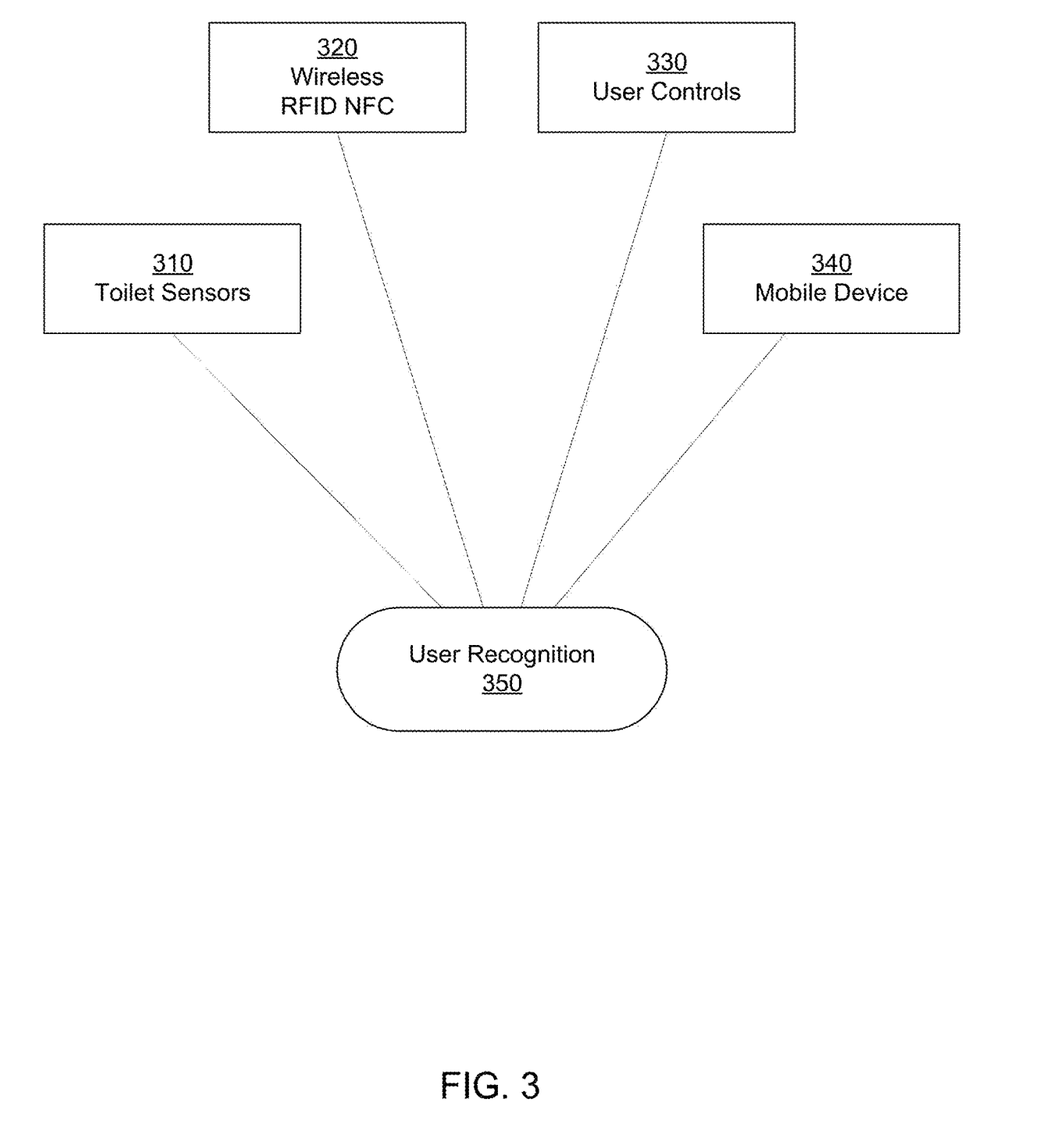
FIG. 3 illustrates a diagram of a user recognition system in an embodiment of the disclosed health monitoring system.

The toilet system may include sensors which recognize that a user has approached and may recognize the identity of the user so as to store data collected in the user's file in the controller and/or apply customized user settings of the wand. FIG. 3 provides a diagram of possible ways that a user may be recognized by the toilet system. Toilet sensors 310 may be located on or in a toilet seat, or be mounted or attached or inside of any part of the toilet apparatus. The sensor may comprise one or more of the following: optical sensors, impedance sensors, electrocardiogram (EKG) sensors, body weight sensors, temperature sensors, pressure sensors, acoustic sensors, audio sensors, microphones, wireless transceivers, cameras, proximity sensors, infrared sensors, biometric sensors, fingerprint sensors, and retinal and/or iris scan sensors. These sensors may recognize a user approaching a toilet and activate a toilet controller input sequence for further recognizing a user. For example, a user may approach a toilet and a proximity sensor may awaken a Bluetooth transceiver or a wireless access point which then may, in turn, activate a software application on a user's mobile device. In another example, a microphone may pick up sound, including a voice command or voice recognition, activate a controller, and query a user wirelessly or visually. In another example, a user sits on an instrumented toilet seat and a user's customized user settings and profile are recognized based on body weight, pulse rate, body temperature, bio-impedance, IP address, mobile device identification (ID), phone number, email address, user login, mac address, and/or EKG readings. Customized user settings are then downloaded from an online database into the controller or uploaded from the program memory of the controller for use. The customized user settings may be used to instruct the wand and its sensors to conduct a specific analysis and position the wand in a manner customized for the user. Any combination of the toilet sensors may be used to recognize a user and associate the identification with customized user settings. A user may have an online or local account for storing customized settings and for recording trending data related to the sensors.

Again, referring to FIG. 3, wireless sensors 320 may comprise a smartcard, radio frequency identification (RFID) chip or tag, or near field communication (NFC) transaction device. For example, a user may register a smartcard with an online or local account. When the user approaches a toilet system according to the instant disclosure in a public restroom, his/her customized user settings may be loaded by interrogating the smartcard. This interrogation may happen when the smartcard is placed in close proximity to a detector on the toilet or elsewhere in the restroom. A barcode may also be read to select and upload a user's customized user settings. In an example, a user has a saved barcode on his/her phone. An optical scanner reads the barcode and then identifies and uploads the customized user settings associated with the barcode.

User controls 330 refers to a manual wand control device which may be input panel 104 shown in FIGS. 1 and 2. In other embodiments, a user may be recognized by a finger print scanner, a camera for optical recognition of a user, or a built-in microphone for voice recognition and command and control functions of the toilet device. In some embodiments, the user may communicate his/her identity to the toilet through the user's mobile device 340, which may be a smartphone or tablet.

Figure 4:
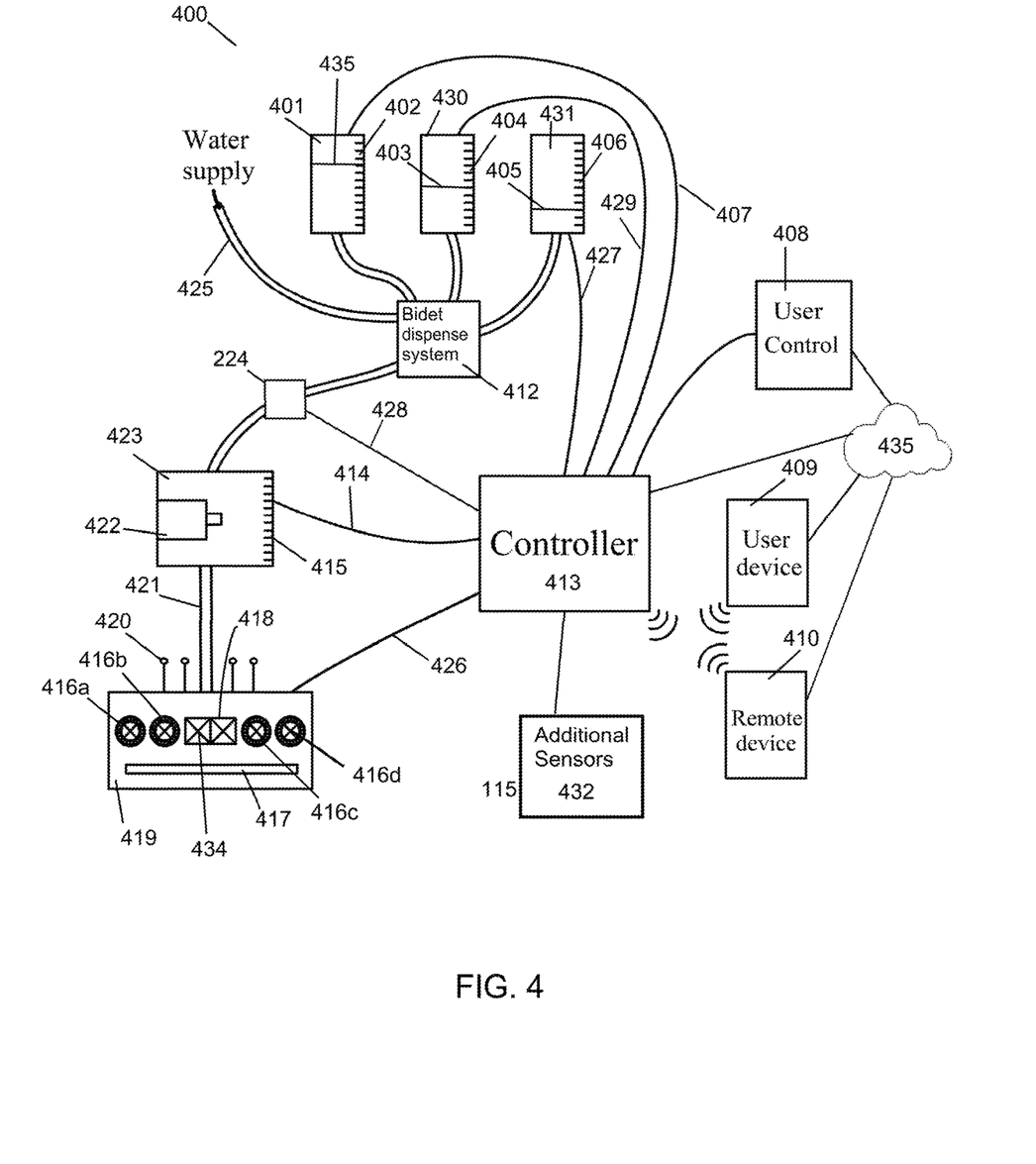
FIG. 4 illustrates schematic diagram of embodiment of the disclosed health monitoring system.

FIG. 4 shows an overall schematic diagram 400 of the toilet system in accordance with an embodiment of the current disclosure. In this embodiment, controller 413 is capable of processing programmed data functions in relation to inputs and outputs of the controller. Controller inputs and outputs may be analog, digital, optical, wireless, Bluetooth, USB, Ethernet, video, audio or acoustic. The controller may be connected to a network of toilet systems, each according to the disclosure, and may be used as an Internet access point for users and for other toilet systems. Dispensing system 412 dispenses water from water supply 425 and reservoir substances 435, 403 and 405 in accordance with user preferences or customized user settings. Sensor module 224 contains sensors for providing feedback to controller 413 through connection 428. The sensors within sensor module 224 may include pressure sensors, temperature sensors, and flow sensors. Wand positioning system 423 positions and tracks head section 419 and is in connection with controller 413 through connection 414. Wand positioning system 423 contains wand movement device 422 for moving the head section 419 to different positions based on user identification, user preferences, gender, detection of a cleansing need, a calendar date, an automatic profile configuration, or a manual selection. The wand movement device 422 may comprise motors, linear actuators, screw drives, solenoids, belt drives, direct drives, pinion gears, or manual actuation, etc. wand positioning system 423 contains position sensors 415 for determining and tracking a position of head section 419. Position sensors 415 may include one or more of the following: Hall sensors, encoders, optical flags, magnetic sensors, magnetic strip sensors, optical graduations, and step counting. Wand positioning system 423 may also contain one or more heaters for heating a substance being dispensed. The position information may be used as feedback control for wand movement device 422 by way of controller 413. Controller 413 may control wand movement device 422 based on position sensors 415 and customized user settings. User device 409 may be a phone, tablet, or computer which connects to controller 413. User device 409 may be used to setup an account for the user containing stored customized user settings. A user account and customized user settings may be stored in the user device 409, controller 413, remote device 410 and/or network database server 435. In addition to sensors on the wand, a user device 409, remote device 410, or user control 408 may be use as an optical inspection device for clinical purposes. Images and or video may be stored and uploaded to network database server 435. A healthcare practitioner may be given access to stored or real time data for clinical purposes. Remote device 410 may be a maintenance computer or a healthcare provider's computer. A healthcare provider may be able to check on a healing surgery, stitches, hemorrhoids, bed sores, etc., and apply medications remotely. Head section 419 may include an inspection system 434 and 418. The inspection system may include cameras, including visible light, video, and infrared cameras and may also include light sources. The light sources may be positioned on the head section 419, on the rigid body section of the wand, or elsewhere within the toilet bowl to provide light to the sensor on the wand. The inspection system may include a fiber optic bundle of transmit receive pairs or a single monofilament transmit and a single monofilament receive pair. Optical lenses may be used which allow for focusing and detection of features of a user's urogenital, perineal, or anal region. Infrared sensors may be used to determine the body temperature of the user, localized temperature in a certain anatomical region, temperature of the user's waste, and the temperature of the water in the toilet bowl. A lens cleaning routine may be used to spray off the lens with water, cleaner or compressed air or heated compressed air. Air or water jets may be formed in a fixed or moveable position on head section 419 for cleaning the inspection optics, camera, or spray ports on head section 419.

FIG. 4 shows four spray ports 416*a*.416*b*, 416*c*, and 416*d*. The spray ports 416*a-d* may be each individually rotatable so as to direct a spray pattern toward a desired area on a user or on a bowl. Controller 413, by way of control line 426, is able to electro-magnetically move each spray port 416*a-d*. Spray ports 416*a-d* may dispense cleansing or therapeutic substances housed in reservoirs 401, 430, and 431. A sheet of water may be dispensed from water dispenser 417. Control line 426 may also carry power, optical signals, and other sensors signals from sensors 420. Sensors 420 may include temperature sensors, pressure sensors, and flow sensors. A head self-cleaning routine may be used automatically inspect and clean the head at the end of each use. A bowl self-cleaning routine may be used to automatically inspect and clean the toilet bowl. The positioning system 423 may be used to rotate head section 419 between 0 and 360 degrees (as shown in FIG. 2) and point towards the inside of the toilet bowl for bowl inspection and cleaning purposes. Additional sensors 432 may be located at different locations other than on the head section 419 on the toilet apparatus. Sensors 432 may include one or more of gas sensors, LEDs, photodiodes, CCD sensors, motion sensors, microphones, and speakers. Controller 413 may read reservoir levels 435, 403, and 405 using level sensors 402, 404, and 406 by way of connections 427, 429, and 407. The controller 413 or a program running on network database server 435 may predict a date of an empty state of reservoirs 401, 430, and 431 based on current, historic and/or trending level sensor readings.

Figure 5A:
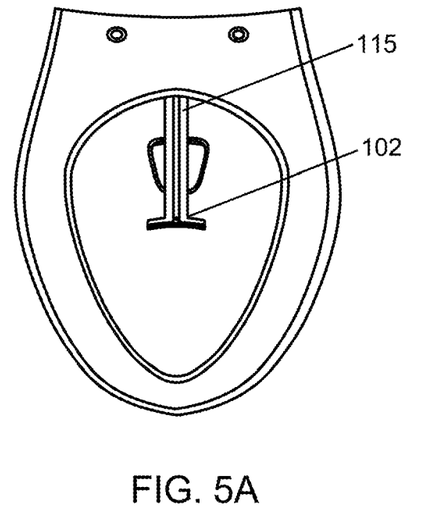
FIGS. 5A, 5B, and 5C illustrate the wand in three different levels of extension.
Figure 5B:
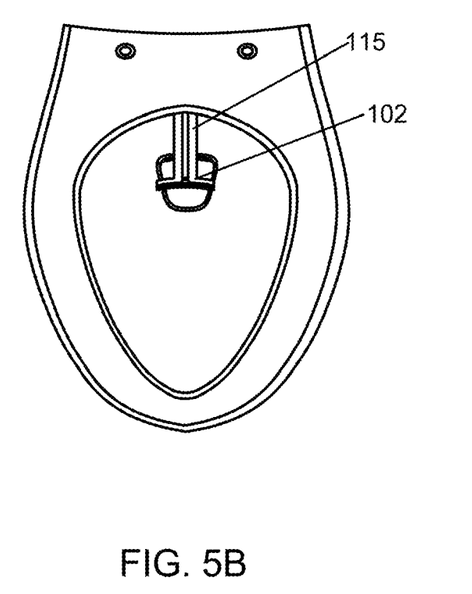
Figure 5C:
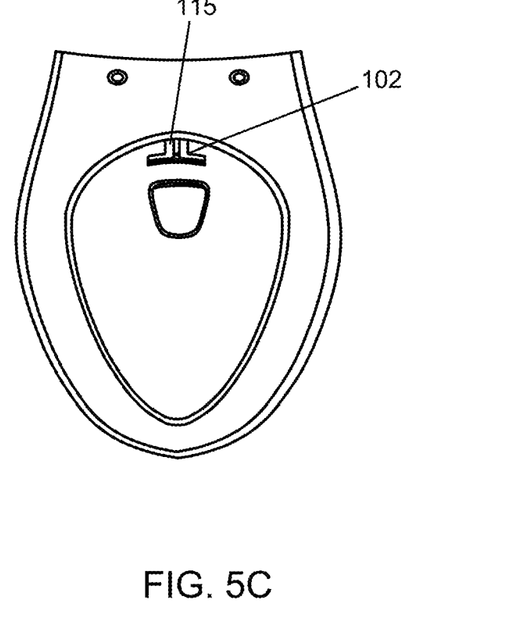

FIGS. 5A, 5B, and 5C illustrate a wand, including head section 102 and ridged body section 115, in positions including three different points of extension. FIG. 5A shows the wand in a fully extended position as may be useful for inspecting and monitoring a front portion of a user's urogenital region and may have specific application for observing a female anatomy. FIG. 5B shows the wand in a partially extended position as may be useful for inspecting a user's anal region. FIG. 5C shows the wand in a fully retracted position, possibly as may occur when the toilet system is not in use.

Figure 6:
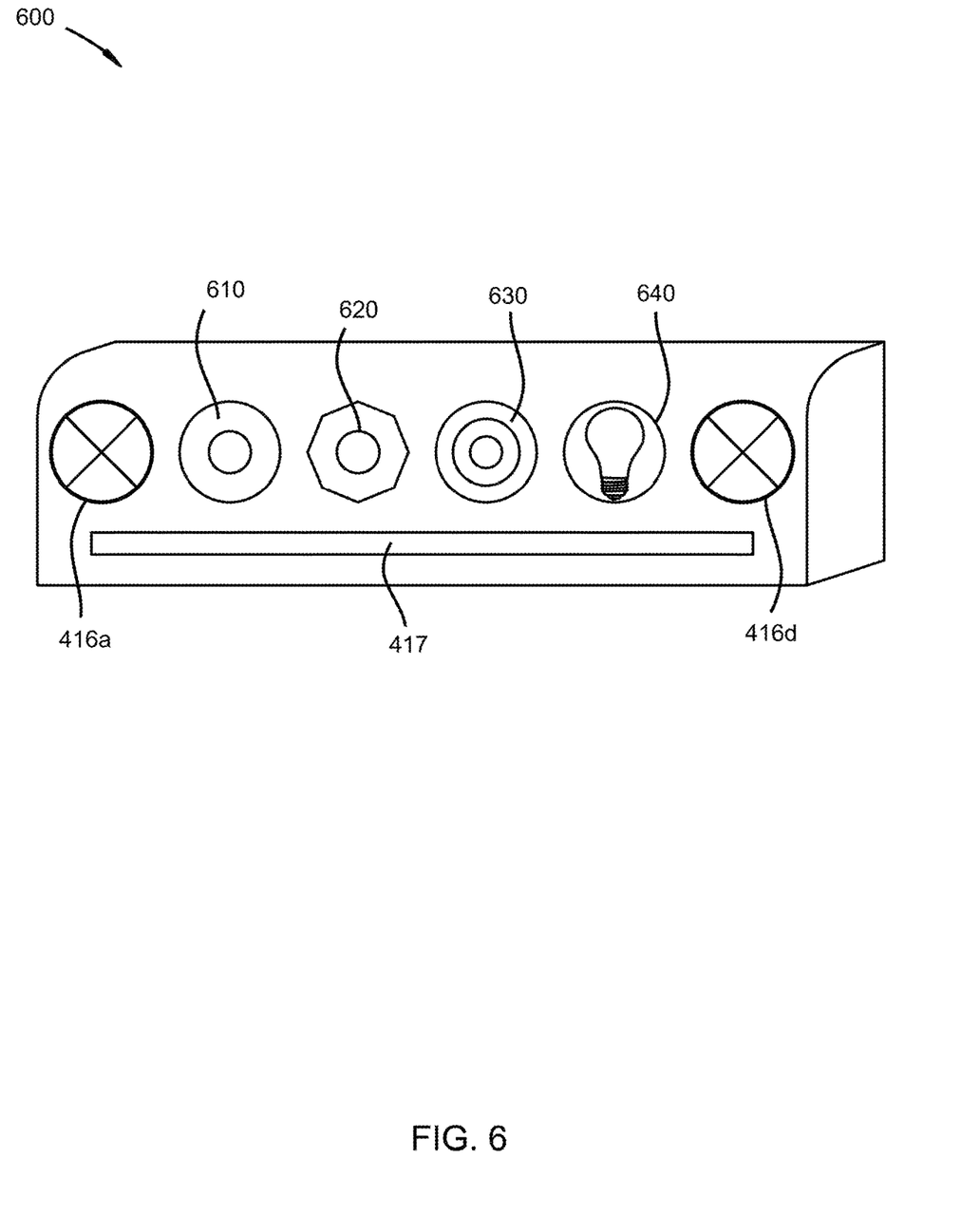
FIG. 6 illustrates a close-up isometric view of an embodiment of a wand head section including sensors and dispensers.

FIG. 6 illustrates a close-up isometric view of head section 600 of a wand with sensors and dispensers which may be included according to the disclosure. As in the head section of FIG. 4, the head section 600 includes spray ports 416*a* and 416*d* which may dispense cleansing or therapeutic substances. A sheet of water may be dispensed from water dispenser 417. Still camera 610 may take photographs using visual light. Infrared camera 620 may be used for thermal imaging. Video camera 360 may be used to illustrate movement, particularly during waste expulsion. Light source 640 may provide added light to assist data collection by still camera 610 or video camera 630.

We claim:

1. A health monitoring toilet system comprising:
   a. a wand, wherein the wand is extendible, retractable, and rotatable;

b. one or more sensor, wherein the one or more sensor is disposed on the wand, and wherein the one or more sensor comprises an infrared sensor configured to measure one or more of the following temperatures: a localized temperature on a user's anatomy, a temperature of the user's waste; and a temperature of the water in the toilet bowl;

c. a controller, wherein the controller receives and processes data from the one or more sensor;

d. a non-transitory computer readable medium, wherein the non-transitory computer readable medium is in connection with the controller through an electronic connection, and wherein the non-transitory computer readable medium stores data associated with a user; and e. a toilet bowl, the toilet bowl comprising a volume of toilet water and a temperature monitor, wherein the temperature monitor is in thermal communication with the volume of toilet water.

2. The health monitoring toilet system of claim 1, wherein the one or more sensor comprises at least one camera.

3. The health monitoring toilet system of claim 2, wherein the at least one camera comprises an infra-red camera.

4. The health monitoring toilet system of claim 1, wherein the one or more sensor comprises a digital imaging device.

5. The health monitoring toilet system of claim 1, wherein the one or more sensor comprises a gas sensor, wherein the gas sensor detects volatile organic compounds.

6. The health monitoring toilet system of claim 1, wherein the one or more sensor comprises a motion video camera.

7. The health monitoring toilet system of claim 1, further comprising a light source.

8. The health monitoring toilet system of claim 7, wherein the light source is disposed on or within the wand.

9. The health monitoring toilet system of claim 1, wherein the wand comprises a bidet wand.

10. The health monitoring toilet system of claim 9, further comprising a wand positioning system, the wand positioning system comprising a wand movement device, wherein the wand movement device comprises a motor, and wherein the non-transitory computer readable medium, actuates the motor and directs movement of the wand.

11. The health monitoring toilet system of claim 10, wherein the wand movement device further comprises one or more of the following: a linear actuator, a screw drive, a solenoid, a belt drive, a direct drive, and a pinion gear.

12. The health monitoring toilet system of claim 10, wherein the wand movement device further comprises a manual control input interface.

13. The health monitoring toilet system of claim 10, further comprising at least one wand movement protocol, wherein the at least one wand movement protocol is stored the non-transitory computer readable medium.

14. The health monitoring toilet system of claim 13, wherein the at least one wand movement protocol is defined for each user as a customized user setting.

15. The health monitoring toilet system of claim 13, wherein the at least one wand movement protocol is defined for either a male or a female user.

16. The health monitoring toilet system of claim 10, wherein the controller is accessible to a healthcare provider, and wherein the healthcare provide has access to modify the wand movement protocol.

17. The health monitoring toilet system of claim 1, wherein the electronic connection between the non-transitory computer readable medium and the controller consists of one of the following: a wireless connection, a wired connection, an optical connection, and a remote network connection.

18. The health monitoring toilet system of claim 1, further comprising:
a. one or more liquid reservoirs; and
b. one or more spray ports, wherein the one or more spray ports are disposed on the wand, and wherein the one or more spray ports are in fluid communication with the one or more liquid reservoirs.

19. The health monitoring toilet system of claim 1, further comprising:
a. a toilet, the toilet comprising a toilet seat;
b. a temperature monitor, wherein the temperature monitor is disposed within the toilet seat.

* * * * *